United States Patent
Ratan et al.

(10) Patent No.: US 9,795,587 B2
(45) Date of Patent: Oct. 24, 2017

(54) COMPOUNDS FOR ENHANCING HYPOXIA INDUCIBLE FACTOR ACTIVITY AND METHODS OF USE

(71) Applicant: Cornell Research Foundation, Inc., Ithaca, NY (US)

(72) Inventors: Rajiv R. Ratan, Scarsdale, NY (US); Ambreena Siddiq, White Plains, NY (US); Juan Chavez, White Plains, NY (US)

(73) Assignee: CORNELL RESEARCH FOUNDATION, INC., Ithaca, NY (US)

( * ) Notice: Subject to any disclaimer, the term of this patent is extended or adjusted under 35 U.S.C. 154(b) by 0 days.

(21) Appl. No.: 14/575,387

(22) Filed: Dec. 18, 2014

(65) Prior Publication Data

US 2015/0258058 A1    Sep. 17, 2015

Related U.S. Application Data

(63) Continuation of application No. 12/083,891, filed as application No. PCT/US2006/041179 on Oct. 20, 2006, now abandoned.

(60) Provisional application No. 60/729,059, filed on Oct. 21, 2005.

(51) Int. Cl.
| | |
|---|---|
| *A61K 31/352* | (2006.01) |
| *A61K 31/343* | (2006.01) |
| *A61K 31/24* | (2006.01) |
| *A61K 31/58* | (2006.01) |

(52) U.S. Cl.
CPC ............ *A61K 31/352* (2013.01); *A61K 31/24* (2013.01); *A61K 31/343* (2013.01); *A61K 31/58* (2013.01)

(58) Field of Classification Search
None
See application file for complete search history.

(56) References Cited

U.S. PATENT DOCUMENTS

| | | |
|---|---|---|
| 6,524,616 B1 | 2/2003 | Notelivitz et al. |
| 6,562,799 B1 | 5/2003 | Semenza |
| 6,828,456 B2 | 12/2004 | Hansen, Jr. et al. |
| 2003/0018007 A1 | 1/2003 | Gregory et al. |

OTHER PUBLICATIONS

Stroke Association, "Stroke Treatments", May 23, 2013, 2 pages, downloaded on Sep. 23, 2016 from: "www.strokeassociation.org/STROKEORG/AboutStroke/Treatment/Stroke-Treatments_UCM_310892_Articlejsp".*
Sangla et al., "Neurocysticerocosis Related Ischaemic Stroke", Revue Neurologique (Paris), 1995, vol. 151(4), pp. 277-280; Abstract only.
Jha et al., "Neurocysticerocosis Presenting as Stroke", Neurology India, 2000, vol. 48(4), pp. 391-394, renumbered 1-3.
Dow et al., Experimental Parasitology, vol. 94, 2000, pp. 259-263.
WHO, WHO Regional Publications, South Asia Series, "The Clinical Management of Acute Malaria", No. 9, 1990, pp. 1-135.
Oliviero et al., Italian Heart Journal, 2000, vol. 1(6), pp. 431-434; Abstract only.
Bakaris et al., Annals of Tropical Paediatrics, 2003, vol. 23(4), pp. 313-317; Abstract only.
Yereli et al., Clinical Microbiology and Infection, 2004, vol. 10(6), pp. 527-529; Abstract only.
Bracken et al., CMLS, Cell Mol. Life Sci., vol. 60, 2003, pp. 1376-1393.

* cited by examiner

*Primary Examiner* — Savitha Rao
*Assistant Examiner* — Gregg Polansky
(74) *Attorney, Agent, or Firm* — Hoffmann & Baron, LLP

(57) ABSTRACT

The present invention relates to methods for enhancing Hypoxia inducible factor-1 (HIF) activity in a cell by contacting the cell with any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analog R-9536-DA, indoprofen, ciclopiroxolamine, tryptophan, ansindione, nabumetone, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, daidzein, tripelennamine citrate, colchicines, aminopyridine, trimethoprim, helenine, hydroxyurea, amiodarone hydrochloride, clindamycin hydrochloride, sulfachlorpyridazine, mephenesin, semustine, clofivric acid, clofibrate, ibuprofen, hyoscyamime, nafcillin sodium, piperin, clidinium bromide, trioxsalen, hydralazine and HIF alpha protein fused to a carrier peptide.

5 Claims, 16 Drawing Sheets

Figure 1A
| Name | Structure |
|---|---|
| 3,6-bis[2-(dimethylamino)ethoxy]-9h-xanthen-9-one dihydrochloride (or tilorone analogue R-10,874-DA) | 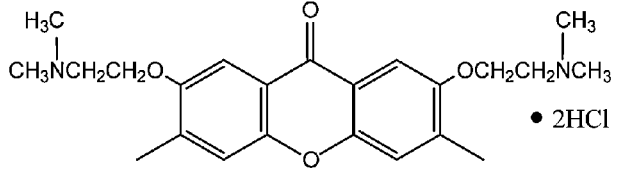 |
| 2,8-bis[dimethylaminoacetyl]dibenzofurin dihydrochloride hydrate (or tilorone analogue R-11,567-DA) | 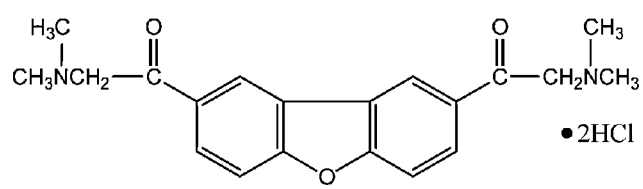 |
| Tilorone analogue R-9536-DA | 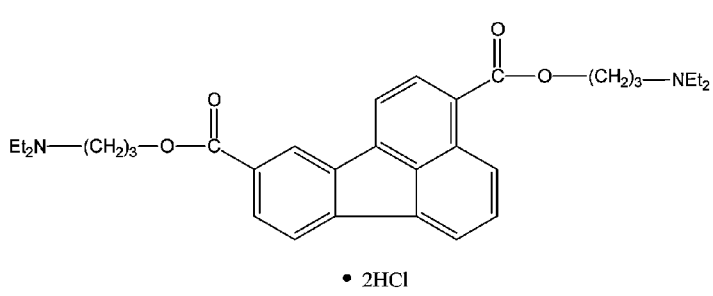 |
| Indoprofen | 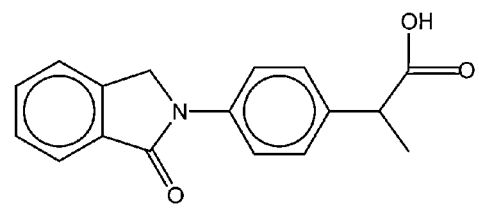 |

Figure 1B
| Name | Structure |
|---|---|
| Ciclopiroxolamine | 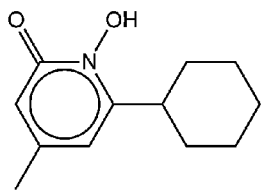 |
| Tryptophan | 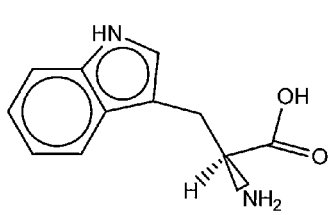 |
| Anisindione | 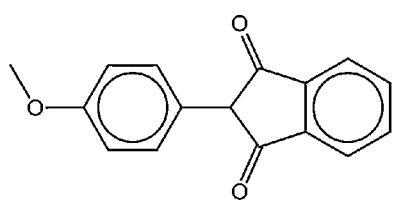 |
| Nabumetone | 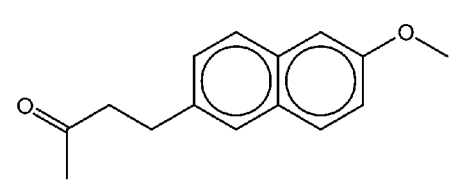 |
| Oxybendazole (or oxibendazole) | 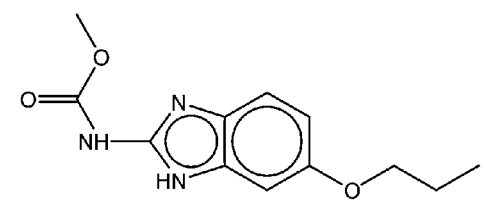 |

Figure 1C

| Name | Structure |
|---|---|
| Albendazole | 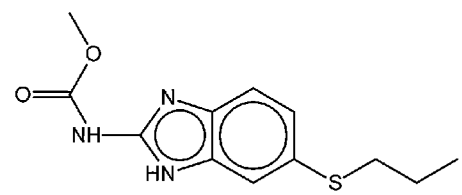 |
| Tropicamide | 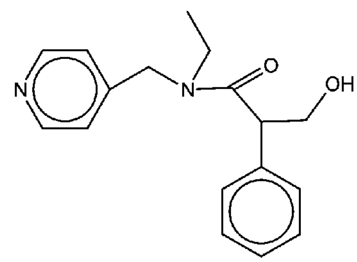 |
| Pramoxine hydrochloride | 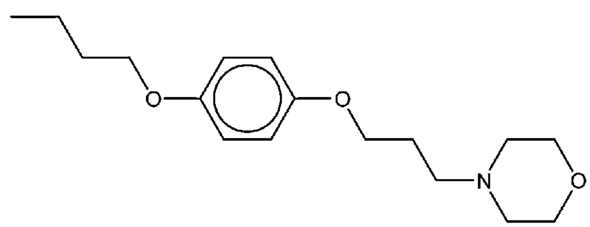 |
| Atenolol | 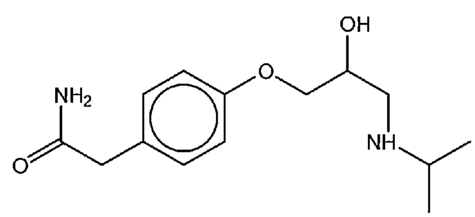 |
| Mebendazole | 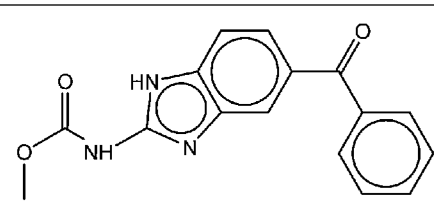 |

Figure 1D

| Name | Structure |
|---|---|
| Carbetapentane citrate | 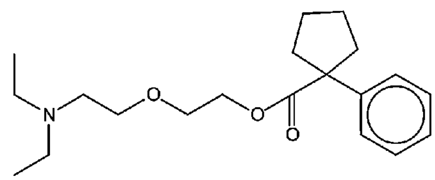 |
| Monensin sodium | 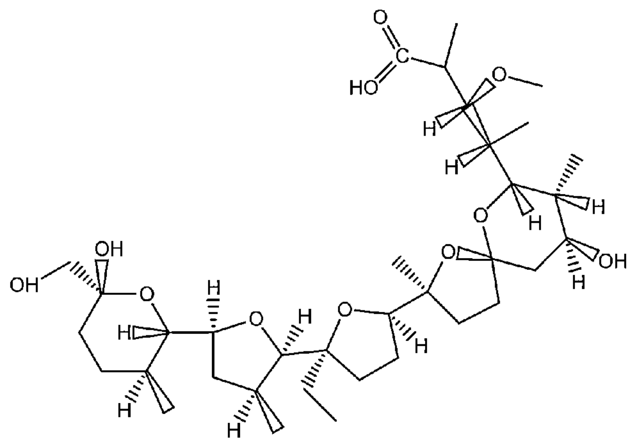 |
| Methoxyvone (or 7-methoxy-5-methyl-2-phenyl-chromen-4-one; or 5-Methyl-7-methoxyisoflavone or Methoxyisoflavone) | 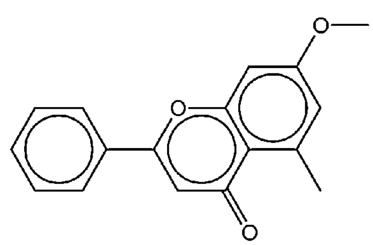 |
| Hydroxyzine pamoate (or atarax; hy-pam 25; hydroxyzine hydrochloride; hydroxyzine pamoate; orgatrax; vistaril) | 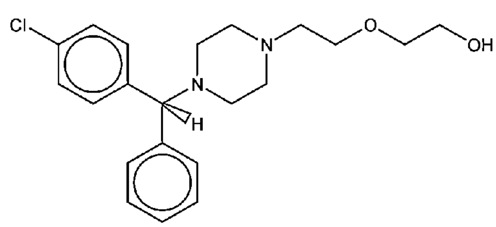 |
| Phenazopyridine (or Phenazopyrinine hydrochloride) | 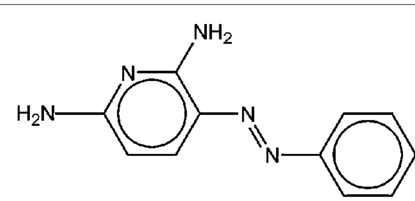 |

Figure 1E
| Name | Structure |
|---|---|
| Clofoctol (or octofene) | 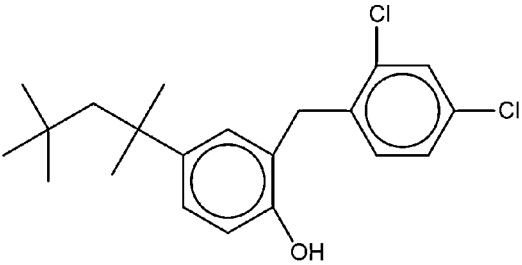 |
| Ipraflavone (or ipriflavone) | 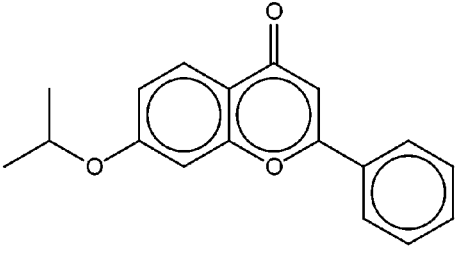 |
| Zomepirac sodium (zomax) | 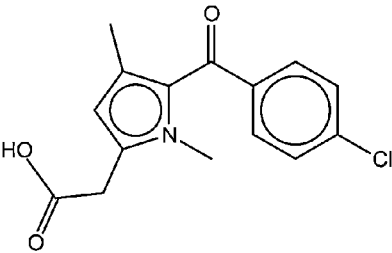 |
| Biochanin A | 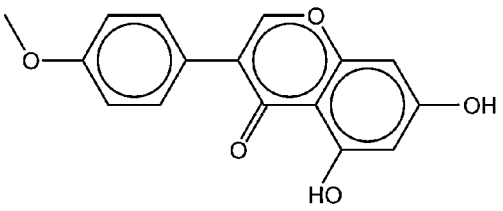 |
| Xylometazoline hydrochloride | 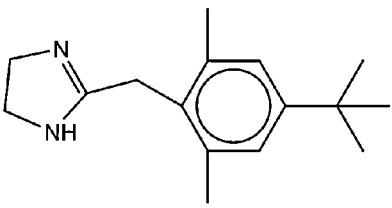 |

Figure 1F
| Name | Structure |
|---|---|
| Fenbendazole | 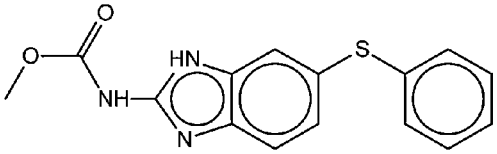 |
| Pirenzepine hydrochloride | 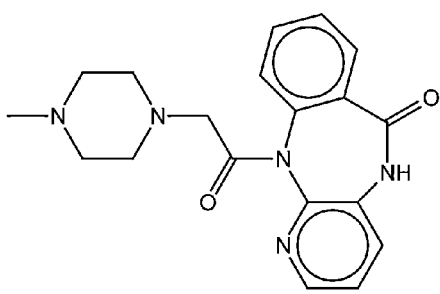 |
| Triprolidine hydrochloride | 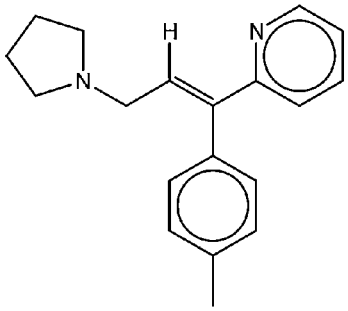 |
| Daidzein | 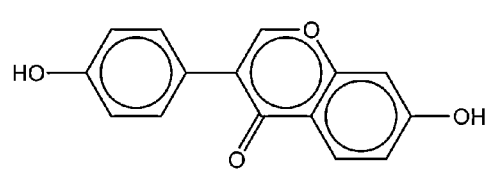 |
| Tripelennamine citrate | 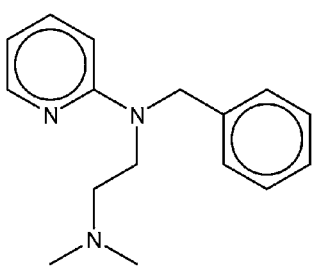 |

Figure 1G

| Name | Structure |
|---|---|
| Colchicine | 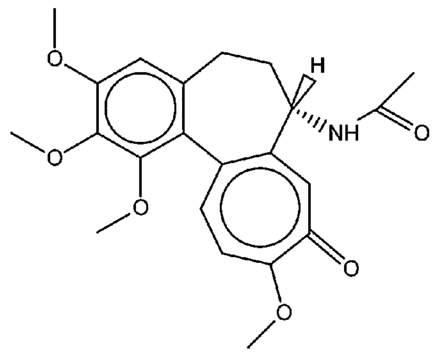 |
| Aminopyridine | 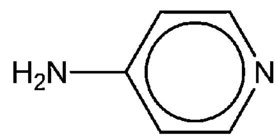 |
| Trimethoprim | 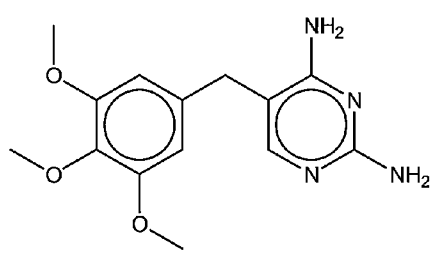 |
| Helenine | 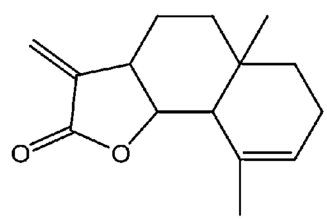 |
| Hydroxyurea | 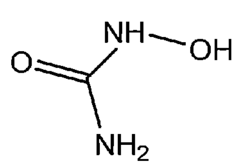 |

Figure 1H
| Name | Structure |
|---|---|
| Amiodarone hydrochloride | 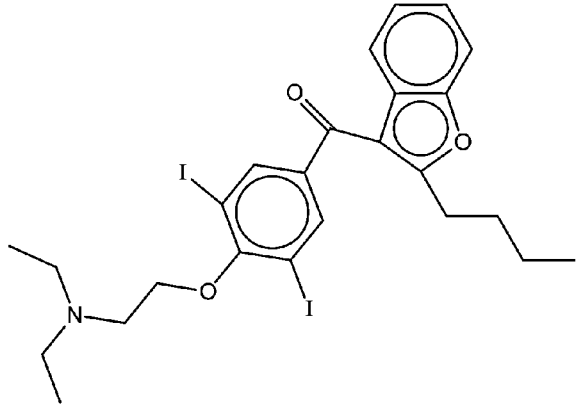 |
| Clindamycin hydrochloride | 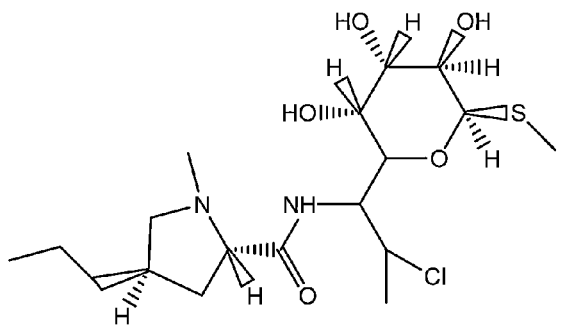 |
| Sulfachlorpyridazine | 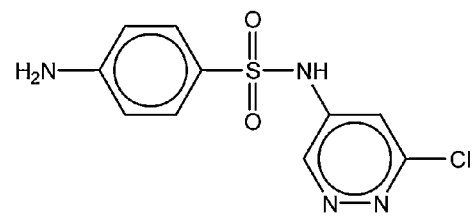 |
| Mephenesin (or myanesin) | 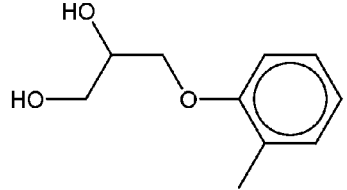 |

Figure 1I

| Name | Structure |
|---|---|
| Semustine | 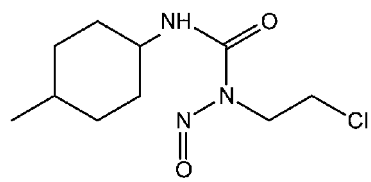 |
| Clofibric acid (or Propionic acid; clofibrin) | 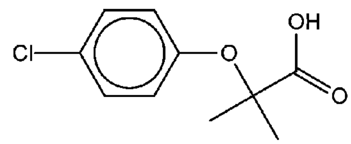 |
| Clofibrate | 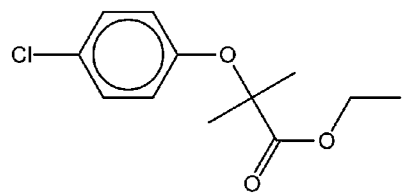 |
| Deferoxamine Mesylate (desferal) | 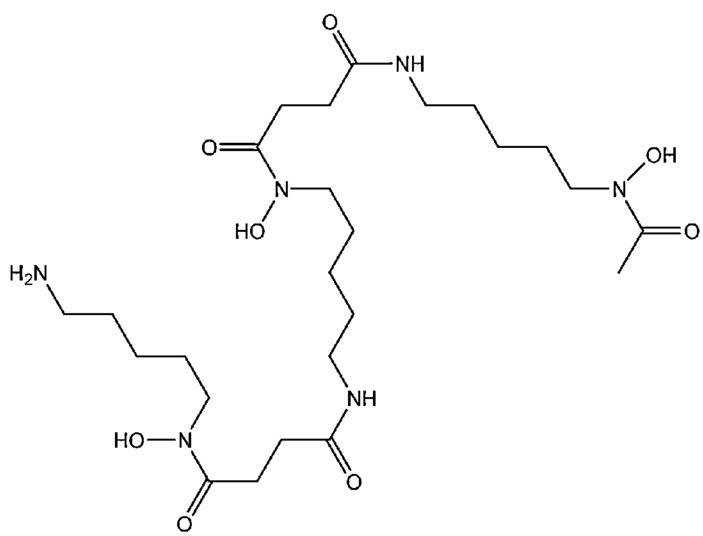 |
| Ibuprofen | 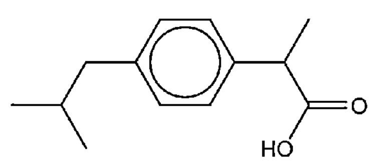 |

Figure 1J

| Name | Structure |
|---|---|
| Hyoscyamine (Levsin, Anaspaz Levbid Levsinex NuLev) | 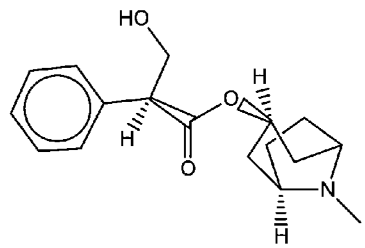 |
| Nafcillin sodium | 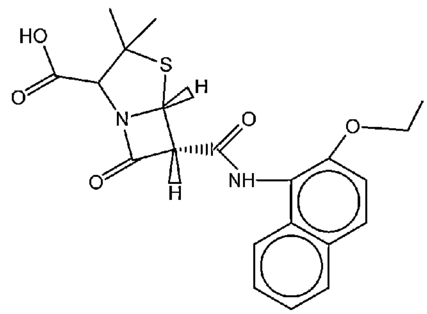 |
| Piperin | 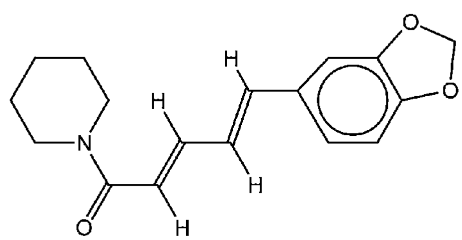 |
| Clidinium bromide | 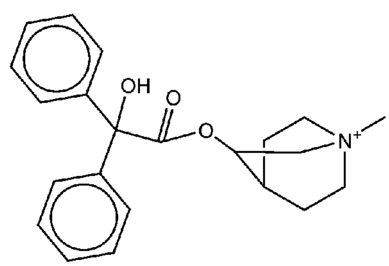 |
| Trioxsalen (or "Trioxsalem") | 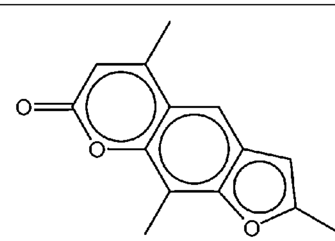 |

| Name | Structure |
|---|---|
| Hydralazine | 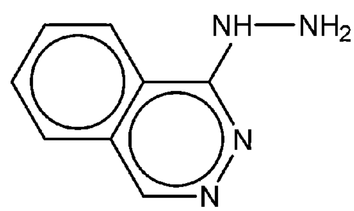 |

Figure 2

```
  1 MEGAGGANDK KKISSERRKE KSRDAARSRR SKESEVFYEL AHQLPLPHNV SSHLDKASVM
 61 RLTISYLRVR KLLDAGDLDI EDDMKAQMNC FYLKALDGFV MVLTDDGDMI YISDNVNKYM
121 GLTQFELTGH SVFDETHPCD HEEMREMLTH RNGLVKKGKE QNTQRSFFLR MKCTLTSRGR
181 TMNIKSATWK VLHCTGHIHV YDTNSNQPQC GYKKPPMTCL VLICEPIPHP SNIEIPLDSK
241 TFLSRHSLDM KFSYCDERIT ELMGYEPEEL LGRSIYEYYH ALDSDHLTKT HHDMFTKGQV
301 TTGQYRMLAK RGGYVWVETQ ATVIYNTKNS QPQCIVCVNY VVSGIIQHDL IFSLQQTECV
361 LKPVESSDMK MTQLFTKVES EDTSSLFDKL KKEPDALTLL APAAGDTIIS LDFGSNDTET
421 DDQLEEVPL YNDVMLPSPN EKLQNINLAM SPLPTAETPK PLRSSADPAL NQEVALKLEP
481 NPESLELSFT MPQIQDQTPS PSDGSTRQSS PEPNSPSEYC FYVDSDMVNE FKLELVEKLF
541 AEDTEAKNPF STQDTDLDLE MLAPYIPMDD DFQLRSFDQL SPLESSSASP ESASPQSTVT
601 VFQQTQIQEP TANATTTTAT TDELKTVTKD RMEDIKILIA SPSPTHIHKE TTSATSSPYR
661 DTQSRTASPN RAGKGVIEQT EKSHPRSPNV LSVALSQRTT VPEEELNPKI LALQNAQRKR
721 KMEHDGSLFQ AVGIGTLLQQ PDDHAATTSL SWKRVKGCKS SEQNGMEQKT IILIPSDLAC
781 RLLGQSMDES GLPQLTSYDC EVNAPIQGSR NLLQGEELLR ALDQVN (SEQ ID NO. 2)
```

COMPOUNDS FOR ENHANCING HYPOXIA INDUCIBLE FACTOR ACTIVITY AND METHODS OF USE

CROSS-REFERENCE TO RELATED APPLICATION APPLICATIONS

This application is a divisional of U.S. patent application Ser. No. 12/083,891, filed Apr. 27, 2009, which is a 371 of PCT/US2006/041179, filed Oct. 20, 2006, which claims the benefit of U.S. Provisional Application No. 60/729,059, filed Oct. 21, 2005. All of the aforementioned applications are incorporated herein by reference in their entireties.

The invention described in this application was made with funds from the National Institutes of Health, Grant Numbers NS 39170, NS 40591, and NS 46239. The United States Government has certain rights in this invention.

The invention was also made with funds from New York State, contract number CO19772. New York State has certain rights in this invention.

BACKGROUND OF THE INVENTION

Hypoxia inducible factor-1 (HIF-1) is a heterodimeric transcriptional activator that regulates the expression of genes involved in adaptation to hypoxic stress. HIF-1 is composed of two subunits referred to as HIF-1α and HIF-1β. These subunits are expressly constitutively. During normal conditions, HIF-1α is targeted to ubiquitination and proteosomal degradation following hydroxylation of HIF-1 at proline 402 and 564 by the enzyme, prolyl hydroxylase.

Prolyl hydroxylases are reported to be oxygen-dependent. For example, under conditions of reduced oxygen, these enzymes function with low efficiency. As a result, HIF-1α is not hydroxylated, and thus not targeted to ubiquitination and degradation. Accordingly, HIF-1α becomes stabilized, and can bind HIF-1β to activate genes involved in adaptation to oxidative stress.

Oxidative stress is reported to be associated with numerous diseases and conditions, including stroke, hypoxia, ischemia, spinal cord injury and neurodegenerative conditions. Thus, compounds which enhance the activity of HIF-1α protein are beneficial for treating conditions and diseases associated with oxidative stress.

SUMMARY OF THE INVENTION

In one embodiment, the present invention relates to a method for enhancing HIF activity in a cell in need thereof. The method comprises contacting the cell with any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, indoprofen, ciclopiroxolamine, tryptophan, ansindione, nabumetone, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, daidzein, tripelennamine citrate, colchicines, aminopyridine, trimethoprim, helenine, hydroxyurea, amiodarone hydrochloride, clindamycin hydrochloride, sulfachlorpyridazine, mephenesin, semustine, clofivric acid, clofibrate, ibuprofen, hyoscyamime, nafcillin sodium, piperin, clidinium bromide, trioxsalen, hydralazine and HIF alpha protein fused to a carrier peptide.

In another embodiment, the invention provides a method for treating a neurodegenerative disease or condition in a mammal in need thereof. The method comprises administering to the mammal any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, ansindione, oxybendazole, tropicamide, mebendazole, carbetapentane citrate, monensin sodium, methoxyvone, hydroxyzine, phenazopyridine, clofoctol, ipraflavone, xylometazoline hydrochloride, fenbendazole, pirenzepine, triprolidine hydrochloride, tripelennamine citrate, colchicines, trimethoprim, helenine, sulfachlorpyridazine, mephenesin, semustine, clofibrate, hyoscyamime, nafcillin sodium, piperin, clidinium bromide, trioxsalen and hydralazine.

In yet another embodiment, the invention provides a method for treating hypoxia in a mammal in need thereof. The method comprises administering to the mammal any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, tryptophan, anisindione, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, daidzein, tripelennamine citrate, colchicine, aminopyridine, trimethoprim, hydroxyurea, amiodarone hydrochloride, clindamycin hydrochloride, sulfachlorpyridazine, mephenesin, semustine, clofibric acid, clofibrate, ibuprofen, hyoscyamime, nafcillin sodium, piperin, clidinium bromide, trioxsalen and hydralazine.

In a further embodiment, the invention provides a method for treating stroke in a mammal in need thereof. The method comprises administering to the mammal any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamime, anisindione, oxybendazole, tropicamide, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, tripelennamine, colchicines, aminopyridine, helenine, sulfachlorpyridazine, mephenesin, semustine, clofibrate, hyoscyamime, nafcillin sodium, piperin, clidinium bromide, trioxalen, and hydralazine.

In yet a further embodiment, the invention provides a method for treating spinal cord injury in a mammal in need thereof. The method comprises administering to the mammal any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, indoprofen, ciclopiroxolamine, anisindione, nabumetone, oxybendazole, tropicamide, pramoxine hydrochloride, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, tripelennamine citrate, colchicines, trimethoprim, helenine, sulfachlorpyridazine, mephenesin, semustine, clofibric acid, clofibrate, deferoxamine mesylate, ibuprofen, hyoscyamime, nafcillin sodium, piperin, clidinium bromide, trioxsalen, and hydralazine.

In another embodiment, the invention provides a method for treating ischemia in a mammal in need thereof. The method comprises administering to the mammal any one of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, tryptophan, anisindione, oxybendazole, tropicamide, pramoxine hydrochloride, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, tripelennamine citrate, colchicine, aminopyridine, hydroxyurea, sulfachlorpyridazine, mephenesin, semustine, clofibrate, hyoscyamime, nafcillin sodium, piperin, clidinium bromide, trioxsalen and hydralazine.

BRIEF DESCRIPTION OF THE FIGURES

FIG. 1A. Chemical structures of 3,6-bis[2-(dimethylamino)ethoxy]-9h-xanthen-9-one dihydrochloride; 2,8-bis[dimethylaminoacetyl]dibenzofurin dihydrochloride hydrate; Tilorone analogue R-9536-DA; Indoprofen.

FIG. 1B. Chemical structures of Ciclopiroxolamine; Tryptophan; Anisindione; Nabumetone; Oxybendazole.

FIG. 1C. Chemical structures of Albendazole; Tropicamide; Pramoxine hydrochloride; Atenolol; Mebendazole.

FIG. 1D. Chemical structures of Carbetapentane citrate; Monensin sodium; Methoxyvone; Hydroxyzine pamoate; Phenazopyridine.

FIG. 1E. Chemical structures of Clofoctol; Ipraflavone; Zomepirac sodium; Biochanin A; Xylometazoline hydrochloride.

FIG. 1F. Chemical structures of Fenbendazole; Pirenzepine hydrochloride; Triprolidine hydrochloride; Daidzein; Tripelennamine citrate.

FIG. 1G. Chemical structures of Colchicine; Aminopyridine; Trimethoprim; Helenine; Hydroxyurea.

FIG. 1H. Chemical structures of Amiodarone hydrochloride; Clindamycin hydrochloride; Sulfachlorpyridazine; Mephenesin.

FIG. 1I. Chemical structures of Semustine; Clofibric acid; Clofibrate; Deferoxamine mesylate; Ibuprofen.

FIG. 1J. Chemical structures of Hyoscyamine; Nafcillin sodium; Piperin; Clidinium bromide; Trioxsalen.

FIG. 2. Amino acid sequence of HIFα protein, NCBI GenBank Accession No. Q16665.

DETAILED DESCRIPTION OF THE INVENTION

Method for Enhancing HIF Activity

Figure 1K:
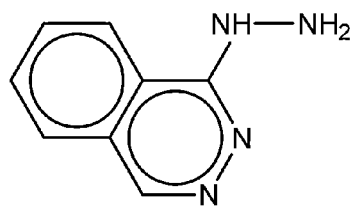
FIG. 1K. Chemical structure of Hydralazine.

In another aspect, the invention provides a method for enhancing HIF activity in a cell in need thereof. The method comprises contacting the cell with an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, indoprofen, ciclopiroxolamine, tryptophan, ansindione, nabumetone, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, daidzein, tripelennamine citrate, colchicines, aminopyridine, trimethoprim, helenine, hydroxyurea, amiodarone hydrochloride, clindamycin hydrochloride, sulfachlorpyridazine, mephenesin, semustine, clofivric acid, clofibrate, ibuprofen, hyoscyamime, nafcillin sodium, piperin, clidinium bromide, trioxsalen, hydralazine and HIFalpha protein fused to a carrier peptide.

The HIF activity can be enhanced in any cell in need thereof. A cell in need of enhancing HIF activity includes cells that are, for example, suffering from trauma, injury, hypoxia, etc. Such cells include those discussed above.

The cell can be contacted with the compound by any method known to those in the art. For example, the cell can be contacted with the compound by incubating the cell and compound in vitro.

Alternatively, the cell can be contacted with the compound in vivo. The compound and cell can be contacted in vivo by any suitable method known to in the art, including the administration methods described below.

Method for Treating Neurodegenerative Disease or Condition

In one aspect, the invention provides a method for treating a neurodegenerative disease or condition in a mammal in need thereof. The method for treating a neurodegenerative disease or condition comprises administering to the mammal an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, ansindione, oxybendazole, tropicamide, mebendazole, carbetapentane citrate, monensin sodium, methoxyvone, hydroxyzine, phenazopyridine, clofoctol, ipraflavone, xylometazoline hydrochloride, fenbendazole, pirenzepine, triprolidine hydrochloride, tripelennamine citrate, colchicines, trimethoprim, helenine, sulfachlorpyridazine, mephenesin, semustine, clofibrate, hyoscyamime, nafcillin sodium, piperin, clidinium bromide, trioxsalen and hydralazine.

Neurodegenerative disease or condition typically refers to a disorder generally characterized by gradual and progressive loss of cells, tissue and/or organ of the central or peripheral nervous system. Examples of such cells, tissues and organs include, the brain, spinal cord, neurons, ganglia, Schwann cells, astrocytes, oligodendrocytes and microglia.

Any mammal suffering from any neurodegenerative disease or condition can be treated in accordance with the method of the present invention. For example, the neurodegenerative disease or condition can be an acute condition. Acute conditions generally occur as a result of trauma to a cell, tissue and/or organ of the nervous system. The trauma can, for example, partially or completely block blood flow to the cell, tissue and/or organ. Examples of acute neurodegenerative conditions include head injury and brain injury.

Alternatively, the neurodegenerative disease or condition can be a chronic neurodegenerative condition. Examples of chronic neurodegenerative diseases and conditions include Parkinson's disease, Alzheimer's disease, Huntington's disease and Amyotrophic Lateral Sclerosis (also known as Lou Gherig's disease).

Method for Treating Hypoxia

In another aspect, the invention provides a method for treating hypoxia in a mammal in need thereof. The method for treating hypoxia comprises administering to the mammal an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, tryptophan, anisindione, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, daidzein, tripelennamine citrate, colchicine, aminopyridine, trimethoprim, hydroxyurea, amiodarone hydrochloride, clindamycin hydrochloride, sulfachlorpyridazine, mephenesin, semustine, clofibric acid, clofibrate, ibuprofen, hyoscyamime, nafcillin sodium, piperin, clidinium bromide, trioxsalen and hydralazine.

Any mammal suffering from hypoxia can be treated in accordance with the method of the present invention. Hypoxia generally refers to a lack of oxygen to cells, organs, and/or tissues. Hypoxia can be caused by, for example, ischemia, anemia and chemical modification of blood, such as carboxyhemoglobin, etc.

Hypoxia can occur in any cell, organ, and/or tissue. Examples of cells, organs, and/or tissues which can be subjected to hypoxia include neuronal cells (e.g., neurons, ganglia, Schwann cells, astrocytes, oligodendrocytes and microglia), brain, spinal cord, kidney cells, intestinal cells, heart and cardiac muscle cells such as myocytes, skin cells, etc.

Method for Treating Stroke

In yet another aspect, the invention provides a method for treating stroke in a mammal in need thereof. The method for treating stroke comprises administering to the mammal an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamime, anisindione, oxybendazole, tropicamide, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, tripelennamine, colchicines, aminopyridine, helenine, sulfachlorpyridazine, mephenesin, semustine, clofibrate, hyoscyamime, nafcillin sodium, piperin, clidinium bromide, trioxalen, and hydralazine.

Any mammal suffering from stroke can be treated in accordance with the method of the present invention. Stroke is a type of cardiovascular disease that generally involves the interruption of blood flow to and/or within the brain. The interruption of blood flow can be due to, for example, a blockage or rupture of an artery or vessel. The blockage typically occurs from a blood clot. As a result of the interruption of blood flow, the brain does not receive sufficient amounts of blood.

Method for Treating Spinal Cord Injury

In a further aspect, the invention provides a method for treating spinal cord injury in a mammal in need thereof. The method for treating spinal cord injury comprises administering to the mammal an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, indoprofen, ciclopiroxolamine, anisindione, nabumetone, oxybendazole, tropicamide, pramoxine hydrochloride, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, tripelennamine citrate, colchicines, trimethoprim, helenine, sulfachlorpyridazine, mephenesin, semustine, clofibric acid, clofibrate, deferoxamine mesylate, ibuprofen, hyoscyamime, nafcillin sodium, piperin, clidinium bromide, trioxsalen, and hydralazine.

Any mammal suffering from spinal cord injury can be treated in accordance with the method of the present invention. The spinal cord is the major bundle of nerves that carry nerve impulses to and from the brain to the rest of the body. The spinal cord is surrounded by rings of bone referred to as vertebra.

Spinal cord injury refers to any damage to the spinal cord. The damage typically results in loss of function, such as mobility or feeling. Damage to the spinal cord can occur, for example, as a result or trauma (car accident, gunshot, falls, etc.) or disease (polio, spina bifida, Friedreich's Ataxia, etc).

Any injury to the spinal cord can be treated in accordance with the method of the present invention. For example, the injury can be a complete injury to the spinal cord. Complete injury typically refers to the lack of function (e.g., no sensation and no voluntary movement) below the site of injury. Both sides of the body are usually affected.

Alternatively, the injury may be an incomplete injury to the spinal cord. An incomplete injury generally refers to some function below the site of injury. For instance, a person with an incomplete injury may be able to move one limb more than another, may be able to feel parts of the body that cannot be moved, or may have more functioning on one side of the body than the other, etc.

Method for Treating Ischemia

In yet a further aspect, the invention provides a method for treating ischemia in a mammal in need thereof. The method comprises administering to the mammal an effective amount of any one, or any combination, of the following compounds: 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, ciclopiroxolamine, tryptophan, anisindione, oxybendazole, tropicamide, pramoxine hydrochloride, mebendazole, carbetapentane citrate, monensin sodium, methoxyvone, hydroxyzine, phenazopyridine, clofoctol, ipraflavone, biochanin A, xylometazoline hydrochloride, fenbendazole, pirenzepine, triprolidine hydrochloride, tripelennamine citrate, colchicine, aminopyridine, hydroxyurea, sulfachlorpyridazine, mephenesin, semustine, clofibrate, hyoscyamime, nafcillin sodium, piperin, clidinium bromide, trioxsalen and hydralazine.

Any mammal suffering from ischemia can be treated in accordance with the method of the present invention. Ischemia generally refers to a condition of decreased blood flow to an organ, tissue and/or cell. The decrease in blood flow can be caused by, for example, constriction (e.g., hypoxemic vasoconstriction) or obstruction (e.g., clot, atherosclerotic plaque) of a blood vessel.

Ischemia can occur in any cell, organ, and/or tissue. Examples of cells, organs, and/or tissues which can be subjected to ischemia include neuronal cells (e.g., neurons, ganglia, Schwann cells, astrocytes, oligodendrocytes and microglia), brain, spinal cord, intestinal cells, kidney cells, heart and cardiac muscle cells such as myocytes, etc.

Compounds

Compounds useful in the methods of the present invention are 3,6-bis[2-(dimethylamino)ethoxy]-9h-xanthen-9-onedihydrochloride, 2,8-bis[dimethylaminoacetyl]dibenzofurin dihydrochloride hydrate, tilorone analogue R-9536-DA, indoprofen, ciclopiroxolamine, tryptophan, ansindione, nabumetone, oxybendazole, albendazole, tropicamide, pramoxine hydrochloride, atenolol, mebendazole, carbetapentane citrate, monensin sodium, methoxyvone, hydroxyzine, phenazopyridine, clofoctol, ipraflavone, zomepirac, biochanin A, xylometazoline hydrochloride, fenbendazole, pirenzepine, triprolidine hydrochloride, daidzein, tripelennamine citrate, colchicines, aminopyridine, trimethoprim, helenine, hydroxyurea, amiodarone hydrochloride, clindamycin hydrochloride, sulfachlorpyridazine, mephenesin, semustine, clofivric acid, clofibrate, ibuprofen, hyoscyamime, nafcillin sodium, piperin, clidinium bromide, trioxsalen, and hydralazine, the chemical structures of which are shown in FIG. 1.

The brand name, generic name, chemical name, alternative spelling, etc. of some of the compounds are listed in FIG. 1. For example, the compound "phenazopyridine hydrochloride" may also be referred to as "phenazopyrinine hydrochloride."

The compounds can be in the form of a pharmaceutically acceptable salt. The term "pharmaceutically acceptable salt" refers to a well-tolerated, nontoxic salt prepared from any one of the compounds mentioned above, and an acid or base. The acids may be inorganic or organic acids of any one of the compounds mentioned above. Examples of inorganic acids include hydrochloric, hydrobromic, nitric hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylenediamine, chloropro-caine, choline, diethanolamine, ethylenediamine, meglumine (N-methylglucamine), and procaine.

Throughout this specification, parameters are defined by maximum and minimum amounts. Each minimum amount can be combined with each maximum amount to define a range.

In one aspect of the invention, the compound is HIF alpha (HIFα) protein fused to a carrier peptide. The HIFα protein portion of the fusion protein can include all of the amino acid sequence of HIFα. The amino acid sequence of HIFα is shown in FIG. 2.

Alternatively, the HIFα protein portion of the fusion protein is a fragment of the amino acid sequence of HIFα containing either one or both prolines at amino acid position numbers 402 and 564 of full length HIFα. Thus, the fragment can be any fragment containing the proline at position 402 and/or position 564 of full length HIFα.

The fragment of HIFα comprises a minimum of four amino acid, preferably about six amino acids, more preferably about eight, even more preferably about twelve, yet even more preferably about fifteen, and most preferably a minimum of about nineteen amino acids. The maximum number of amino acids in the fragment is 825, preferably about 750, more preferably about 600, even more preferably about 500, yet even more preferably about 400, further more preferably about 200, and most preferably a maximum of about 100.

For example, the fragment can comprise the fifteen to nineteen, 31 to 79, or 121 to 200, etc. amino acid sequence corresponding to the residues adjacent to, and/or surrounding, proline residue 402 and/or 564, of HIFα.

In a preferred embodiment, the fragment comprises proline residues 402 and 562 and all residues between the proline residues.

The HIFα portion of the fusion protein can comprise functional analogs of, the entire HIFα amino acid sequence, or fragments described above. The functional analogs must satisfy function and contain either one or both prolines at amino acid position numbers 402 and 564 of full length HIFα. The functional analog may, for example, be a substitution variant of full length HIFα, or a substitution variant of a fragment described above.

Suitable substitution variants of full length HIFα or fragment include conservative amino acid substitutions. Amino acids may be grouped according to their physicochemical characteristics as follows:
 (a) Non-polar amino acids: Ala(A) Ser(S) Thr(T) Pro(P) Gly(G);
 (b) Acidic amino acids: Asn(N) Asp(D) Glu(E) Gln(Q);
 (c) Basic amino acids: His(H) Arg(R) Lys(K);
 (d) Hydrophobic amino acids: Met(M) Leu(L) Ile(I) Val (V); and
 (e) Aromatic amino acids: Phe(F) Tyr(Y) Trp(W) His(H).

Substitutions of an amino acid in a peptide by another amino acid in the same group is referred to as a conservative substitution. Conservative substitutions tend to preserve the physicochemical characteristics of the original peptide. In contrast, substitutions of an amino acid in a peptide by another amino acid in a different group is generally more likely to alter the characteristics of the original peptide.

A carrier peptide, in general, refers to any synthetic or naturally occurring amino acid sequence that can transduce or assist in the transduction of a protein or peptide into a cell. Carrier peptides are also referred to a protein transduction domains.

The carrier peptide portion of the fusion protein can be any protein transduction domain or carrier peptide known to those skilled in the art. Examples of protein transduction domains include HIV tat, herpes simplex virus VP22 transcription factor, and *Drosophila* homeotic transcription factor encoded by antennapedia gene. Such transduction domains are disclosed in Schwarze et al., 2000, *Trends in Pharmacol. Sci.*, 21:45-48.

Other examples of suitable carrier peptides include the protein transduction domains disclosed in U.S. Pat. No. 6,221,355 to Dowdy; U.S. Pat. No. 5,652,122 to Frankel et al. The protein transduction domains of U.S. Pat. Nos. 6,221,355 and 5,652,122 are hereby incorporated by reference.

Further examples of carrier peptides include aromatic-cationic peptides comprising (i) at least one net positive charge, (ii) a minimum of three amino acids, (iii) a maximum of about twenty amino acids, (iv) a relationship between the minimum number of net positive charges ($p_m$) and the total number of amino acid residues (r) wherein $3p_m$ is the largest number that is less than or equal to r+1, and (v) a relationship between the minimum number of aromatic groups (a) and the total number of net positive charges ($p_t$) wherein 3a is the largest number that is less than or equal to $p_t+1$, except that when a is 1, $p_t$ may also be 1.

The definition and description of aromatic-cationic peptides, and tables listing examples of aromatic-cationic peptides are disclosed in U.S. application Ser. No. 10/838,135 filed on May 3, 2004 of Szeto, et al. and assigned to Cornell Research Foundation, Inc. The definition, description, tables and examples of aromatic-cationic peptides disclosed in U.S. application Ser. No. 10/838,135 are hereby incorporated by reference.

For example, the carrier peptide can be any one of the aromatic-cationic peptides shown below in Tables 1 and 2.

TABLE 1

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Tyr | D-Arg | Phe | Lys | | $NH_2$ |
| Tyr | D-Arg | Phe | Orn | | $NH_2$ |
| Tyr | D-Arg | Phe | Dab | | $NH_2$ |
| Tyr | D-Arg | Phe | Dap | | $NH_2$ |
| 2'6'Dmt | D-Arg | Phe | Lys | | $NH_2$ |
| 2'6'Dmt | D-Arg | Phe | Lys | Cys | $NH_2$ (SEQ ID NO: 2) |
| 2'6'Dmt | D-Arg | Phe | Lys-NH(CH$_2$)$_2$—NH-dns | | $NH_2$ |
| 2'6'Dmt | D-Arg | Phe | Lys-NH(CH$_2$)$_2$—NH-atn | | $NH_2$ |
| 2'6'Dmt | D-Arg | Phe | dnsLys | | $NH_2$ |
| 2'6'Dmt | D-Cit | Phe | Lys | | $NH_2$ |
| 2'6'Dmt | D-Cit | Phe | Ahp | | $NH_2$ |
| 2'6'Dmt | D-Arg | Phe | Orn | | $NH_2$ |
| 2'6'Dmt | D-Arg | Phe | Dab | | $NH_2$ |
| 2'6'Dmt | D-Arg | Phe | Dap | | $NH_2$ |
| 2'6'Dmt | D-Arg | Phe | Ahp(2-aminoheptanoic acid) | | $NH_2$ |
| Bio-2'6'Dmt | D-Arg | Phe | Lys | | $NH_2$ |
| 3'5'Dmt | D-Arg | Phe | Lys | | $NH_2$ |
| 3'5'Dmt | D-Arg | Phe | Orn | | $NH_2$ |
| 3'5'Dmt | D-Arg | Phe | Dab | | $NH_2$ |
| 3'5'Dmt | D-Arg | Phe | Dap | | $NH_2$ |
| Tyr | D-Arg | Tyr | Lys | | $NH_2$ |
| Tyr | D-Arg | Tyr | Orn | | $NH_2$ |
| Tyr | D-Arg | Tyr | Dab | | $NH_2$ |
| Tyr | D-Arg | Tyr | Dap | | $NH_2$ |
| 2'6'Dmt | D-Arg | Tyr | Lys | | $NH_2$ |
| 2'6'Dmt | D-Arg | Tyr | Orn | | $NH_2$ |
| 2'6'Dmt | D-Arg | Tyr | Dab | | $NH_2$ |
| 2'6'Dmt | D-Arg | Tyr | Dap | | $NH_2$ |
| 2'6'Dmt | D-Arg | 2'6'Dmt | Lys | | $NH_2$ |
| 2'6'Dmt | D-Arg | 2'6'Dmt | Orn | | $NH_2$ |
| 2'6'Dmt | D-Arg | 2'6'Dmt | Dab | | $NH_2$ |
| 2'6'Dmt | D-Arg | 2'6'Dmt | Dap | | $NH_2$ |
| 3'5'Dmt | D-Arg | 3'5'Dmt | Arg | | $NH_2$ |
| 3'5'Dmt | D-Arg | 3'5'Dmt | Lys | | $NH_2$ |
| 3'5'Dmt | D-Arg | 3'5'Dmt | Orn | | $NH_2$ |
| 3'5'Dmt | D-Arg | 3'5'Dmt | Dab | | $NH_2$ |
| Tyr | D-Lys | Phe | Dap | | $NH_2$ |
| Tyr | D-Lys | Phe | Arg | | $NH_2$ |
| Tyr | D-Lys | Phe | Lys | | $NH_2$ |
| Tyr | D-Lys | Phe | Orn | | $NH_2$ |
| 2'6'Dmt | D-Lys | Phe | Dab | | $NH_2$ |
| 2'6'Dmt | D-Lys | Phe | Dap | | $NH_2$ |
| 2'6'Dmt | D-Lys | Phe | Arg | | $NH_2$ |
| 2'6'Dmt | D-Lys | Phe | Lys | | $NH_2$ |
| 3'5'Dmt | D-Lys | Phe | Orn | | $NH_2$ |
| 3'5'Dmt | D-Lys | Phe | Dab | | $NH_2$ |
| 3'5'Dmt | D-Lys | Phe | Dap | | $NH_2$ |
| 3'5'Dmt | D-Lys | Phe | Arg | | $NH_2$ |
| Tyr | D-Lys | Tyr | Lys | | $NH_2$ |
| Tyr | D-Lys | Tyr | Orn | | $NH_2$ |
| Tyr | D-Lys | Tyr | Dab | | $NH_2$ |
| Tyr | D-Lys | Tyr | Dap | | $NH_2$ |
| 2'6'Dmt | D-Lys | Tyr | Lys | | $NH_2$ |
| 2'6'Dmt | D-Lys | Tyr | Orn | | $NH_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| 2'6'Dmt | D-Lys | Tyr | Dab | | NH$_2$ |
| 2'6'Dmt | D-Lys | Tyr | Dap | | NH$_2$ |
| 2'6'Dmt | D-Lys | 2'6'Dmt | Lys | | NH$_2$ |
| 2'6'Dmt | D-Lys | 2'6'Dmt | Orn | | NH$_2$ |
| 2'6'Dmt | D-Lys | 2'6'Dmt | Dab | | NH$_2$ |
| 2'6'Dmt | D-Lys | 2'6'Dmt | Dap | | NH$_2$ |
| 2'6'Dmt | D-Arg | Phe | dnsDap | | NH$_2$ |
| 2'6'Dmt | D-Arg | Phe | atnDap | | NH$_2$ |
| 3'5'Dmt | D-Lys | 3'5'Dmt | Lys | | NH$_2$ |
| 3'5'Dmt | D-Lys | 3'5'Dmt | Orn | | NH$_2$ |
| 3'5'Dmt | D-Lys | 3'5'Dmt | Dab | | NH$_2$ |
| 3'5'Dmt | D-Lys | 3'5'Dmt | Dap | | NH$_2$ |
| Tyr | D-Lys | Phe | Arg | | NH$_2$ |
| Tyr | D-Orn | Phe | Arg | | NH$_2$ |
| Tyr | D-Dab | Phe | Arg | | NH$_2$ |
| Tyr | D-Dap | Phe | Arg | | NH$_2$ |
| 2'6'Dmt | D-Arg | Phe | Arg | | NH$_2$ |
| 2'6'Dmt | D-Lys | Phe | Arg | | NH$_2$ |
| 2'6'Dmt | D-Orn | Phe | Arg | | NH$_2$ |
| 2'6'Dmt | D-Dab | Phe | Arg | | NH$_2$ |
| 3'5'Dmt | D-Dap | Phe | Arg | | NH$_2$ |
| 3'5'Dmt | D-Arg | Phe | Arg | | NH$_2$ |
| 3'5'Dmt | D-Lys | Phe | Arg | | NH$_2$ |
| 3'5'Dmt | D-Orn | Phe | Arg | | NH$_2$ |
| Tyr | D-Lys | Tyr | Arg | | NH$_2$ |
| Tyr | D-Orn | Tyr | Arg | | NH$_2$ |
| Tyr | D-Dab | Tyr | Arg | | NH$_2$ |
| Tyr | D-Dap | Tyr | Arg | | NH$_2$ |
| 2'6'Dmt | D-Arg | 2'6'Dmt | Arg | | NH$_2$ |
| 2'6'Dmt | D-Lys | 2'6'Dmt | Arg | | NH$_2$ |
| 2'6'Dmt | D-Orn | 2'6'Dmt | Arg | | NH$_2$ |
| 2'6'Dmt | D-Dab | 2'6'Dmt | Arg | | NH$_2$ |
| 3'5'Dmt | D-Dap | 3'5'Dmt | Arg | | NH$_2$ |
| 3'5'Dmt | D-Arg | 3'5'Dmt | Arg | | NH$_2$ |
| 3'5'Dmt | D-Lys | 3'5'Dmt | Arg | | NH$_2$ |
| 3'5'Dmt | D-Orn | 3'5'Dmt | Arg | | NH$_2$ |
| Mmt | D-Arg | Phe | Lys | | NH$_2$ |
| Mmt | D-Arg | Phe | Orn | | NH$_2$ |
| Mmt | D-Arg | Phe | Dab | | NH$_2$ |
| Mmt | D-Arg | Phe | Dap | | NH$_2$ |
| Tmt | D-Arg | Phe | Lys | | NH$_2$ |
| Tmt | D-Arg | Phe | Orn | | NH$_2$ |
| Tmt | D-Arg | Phe | Dab | | NH$_2$ |
| Tmt | D-Arg | Phe | Dap | | NH$_2$ |
| Hmt | D-Arg | Phe | Lys | | NH$_2$ |
| Hmt | D-Arg | Phe | Orn | | NH$_2$ |
| Hmt | D-Arg | Phe | Dab | | NH$_2$ |
| Hmt | D-Arg | Phe | Dap | | NH$_2$ |
| Mmt | D-Lys | Phe | Lys | | NH$_2$ |
| Mmt | D-Lys | Phe | Orn | | NH$_2$ |
| Mmt | D-Lys | Phe | Dab | | NH$_2$ |
| Mmt | D-Lys | Phe | Dap | | NH$_2$ |
| Mmt | D-Lys | Phe | Arg | | NH$_2$ |
| Tmt | D-Lys | Phe | Lys | | NH$_2$ |
| Tmt | D-Lys | Phe | Orn | | NH$_2$ |
| Tmt | D-Lys | Phe | Dab | | NH$_2$ |
| Tmt | D-Lys | Phe | Dap | | NH$_2$ |
| Tmt | D-Lys | Phe | Arg | | NH$_2$ |
| Hmt | D-Lys | Phe | Lys | | NH$_2$ |
| Hmt | D-Lys | Phe | Orn | | NH$_2$ |
| Hmt | D-Lys | Phe | Dab | | NH$_2$ |
| Hmt | D-Lys | Phe | Dap | | NH$_2$ |
| Hmt | D-Lys | Phe | Arg | | NH$_2$ |
| Mmt | D-Lys | Phe | Arg | | NH$_2$ |
| Mmt | D-Orn | Phe | Arg | | NH$_2$ |
| Mmt | D-Dab | Phe | Arg | | NH$_2$ |
| Mmt | D-Dap | Phe | Arg | | NH$_2$ |
| Mmt | D-Arg | Phe | Arg | | NH$_2$ |
| Tmt | D-Lys | Phe | Arg | | NH$_2$ |
| Tmt | D-Orn | Phe | Arg | | NH$_2$ |
| Tmt | D-Dab | Phe | Arg | | NH$_2$ |
| Tmt | D-Dap | Phe | Arg | | NH$_2$ |
| Tmt | D-Arg | Phe | Arg | | NH$_2$ |
| Hmt | D-Lys | Phe | Arg | | NH$_2$ |
| Hmt | D-Orn | Phe | Arg | | NH$_2$ |
| Hmt | D-Dab | Phe | Arg | | NH$_2$ |

TABLE 1-continued

| Amino Acid Position 1 | Amino Acid Position 2 | Amino Acid Position 3 | Amino Acid Position 4 | Amino Acid Position 5 (if present) | C-Terminal Modification |
|---|---|---|---|---|---|
| Hmt | D-Dap | Phe | Arg | | $NH_2$ |
| Hmt | D-Arg | Phe | Arg | | $NH_2$ |

Dab = diaminobutyric
Dap = diaminopropionic acid
Dmt = dimethyltyrosine
Mmt = 2'-methyltyrosine
Tmt = N,2'6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin

TABLE 2

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Dmt | Lys | $NH_2$ |
| Phe | D-Arg | Lys | Dmt | $NH_2$ |
| Phe | D-Arg | Phe | Lys | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexy

Administration

The compounds are administered to a mammal. Any mammal can be treated in accordance with the methods of the present invention. Suitable mammals include, for example farm animals, such as sheep, pigs, cows, and horses; pet animals, such as dogs and cats; laboratory animals, such as rats, mice and rabbits; and primates, such a monkeys and humans. In a preferred embodiment, the mammal is a human.

The compound is administered to the mammal in an amount effective in achieving its purpose. The effective amount of the compound to be administered can be readily determined by those skilled in the art during pre-clinical trials and clinical trials by methods familiar to physicians and clinicians.

In one aspect, the compound is considered to be effective in enhancing HIF activity if the activity of HIF is enhanced by at least about 10%, preferably at least about 25%, more preferably at least about 50%, even more preferably at least about 75%, and most preferably at least about 90%.

The compound can be administered by any method known to those skilled in the art. Some examples of suitable modes of administration include oral and systemic administration. Systemic administration can be enteral or parenteral. Liquid or solid (e.g., tablets, gelatin capsules) formulations can be employed for systemic administration. Parenteral administration of the compound include, for example intravenous, intramuscular, and subcutaneous injections. For instance, a compound may be administered to a mammal by sustained release, as is known in the art. Sustained release administration is a method of drug delivery to achieve a certain level of the drug over a particular period of time.

Other routes of administration include oral, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a compound can be accomplished by a nebulizer or liquid mist.

The compound is preferably in a suitable pharmaceutical composition comprising a pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical composition may also comprises one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the compound.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the pharmaceutical composition in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The pharmaceutical composition may additionally contain one or more conventional additives. Some examples of such additives include a solubilizer such as, for example, glycerol; an antioxidant such as for example, benzalkonium chloride (a mixture of quaternary ammonium compounds, known as "quat"), benzyl alcohol, chloretone or chlorobutanol; anaesthetic agent such as for example a morphine derivative; or an isotonic agent etc., such as those described above. As a further precaution against oxidation or other spoilage, the compound may be stored under nitrogen gas in vials sealed with impermeable stoppers.

EXAMPLES

Example 1: Tilorone Analogues R-10,874-DA, R-11,567-DA, and R-9536-DA Enhances Hypoxia Inducible Factor-1 in the Nervous System HT22 murine hippocampal cells were stably transfected with an enolase 1 promoter-luciferase reporter construct and selected with puromycin. Tilorone analogues R-10,874-DA, R-11,567-DA, and R-9536-DA were tested for their ability to activate a HIF-luciferase reporter. Luciferase activity was measured using a Luciferase Assay System (PROMEGA) according to the manufacture's protocol.

HIF-1α protein levels were determined in nuclear extracts using a monoclonal anti-HIF-1α antibody (NOVUS Biologicals). Real time RT-PCR was performed in a ABI-7500 instruments using commercial Taqman gene expression assays (Applied BioSystems).

Male Sprague Dawley rats, weighing 275-350 gm, were used in these experiments. For surgical procedures, anesthesia was induced with 5% isofluorane delivered in oxygen and maintained at 1.5% throughout surgery. Core body temperature was maintained at 37° C. by a homeothermic heating blanket.

Animals were subjected to MCAo by the intraluminal filament method. The right external carotid artery was ligated, cauterized, and cut, and its branches were coagulated. A 35 mm length of 4-0 nylon monofilament (Ethicon) with a rounded tip was then inserted into the internal carotid artery via the proximal end of the external carotid artery stump. The filament was advanced 20 mm beyond the carotid artery bifurcation with slight resistance was encountered. The tilorone analogues R-10,874-DA, R-11,567-DA, and R-9536-DA were injected 100 mg/kg i.p. 24 h pre-MCAo. Equivalent volume of saline was injected i.p. to control rats. Animals were sacrificed 24 h post-MCAo.

Figure 3:
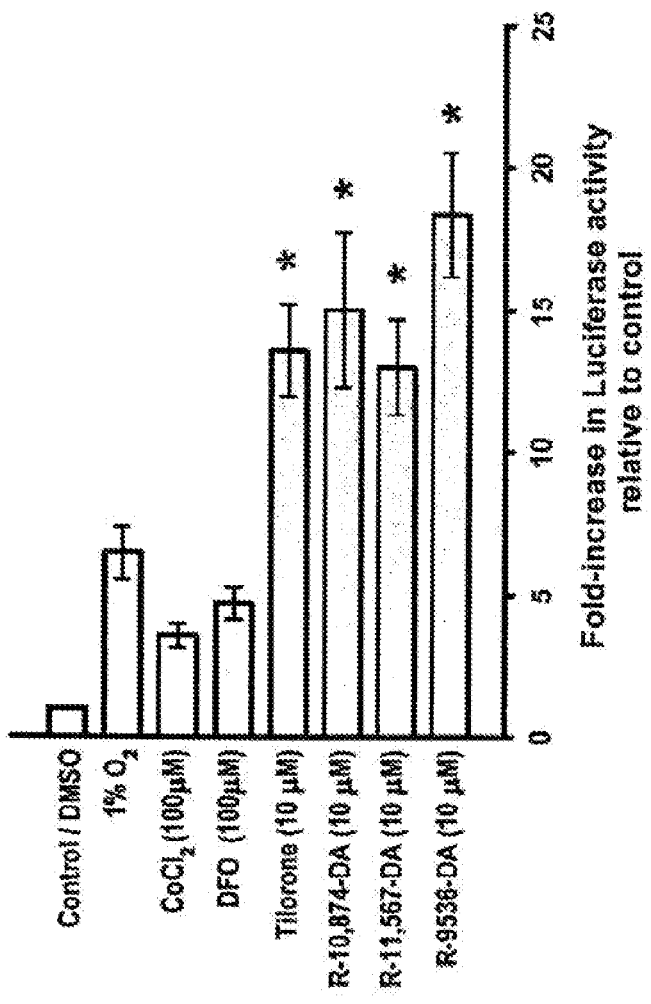
FIG. 3. Tilorone analogues increase HIF-1 transcriptional activity.
Figure 4:
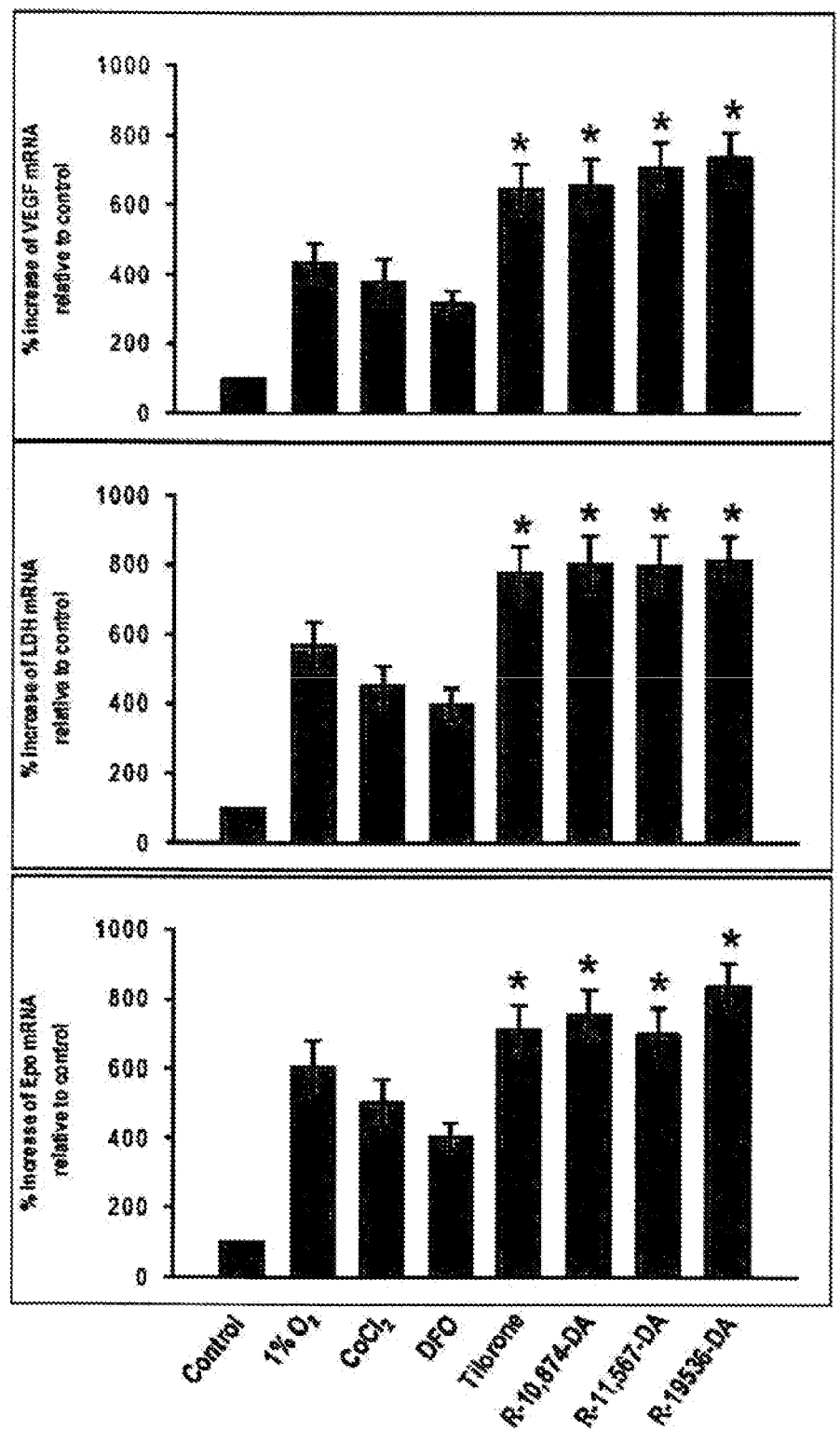
FIG. 4. Tilorone analogues induce the expression of HIF-1 target genes in the rat cerebral cortex.

FIG. 3 shows that tilorone analogues R-10,874-DA, R-11,567-DA, and R-9536-DA increase HIF-1 transcriptional activity. Tilorone analogues R-10,874-DA, R-11,567-DA, and R-9536-DA induce the expression of HIF-1 target genes (FIG. 4) in the rat cerebral cortex.

Example 2: HIF1α/Carrier Peptide Fusion Protein Enhances HIF Activity

The peptide designated HIF/ODD/wt contains part of the oxygen dependent domain, including the C-terminal hydroxylation site of human HIF-1α at proline 564 (DDLDEMLAPYIPMDDDFQL (SEQ ID NO: 3); bold P=proline 564). The HIF/ODD/wt peptide and the peptide control with mutation of both prolines to alanine (HIF/ODD/mut; DDLEMLAAYIAMDDDFQL) (SEQ ID NO: 4) were rendered cell permeant by fusing each of these peptides to the cell-membrane transduction domain of the human immunodeficiency virus-type 1 tat protein (YGRKKKRRQRR) (SEQ ID NO: 5) to obtain two 30 amino acid peptides Tat-HIF/ODD/wt and Tat-HIF/ODD/mut.

To evaluate the ability of Tat-HIF/ODD peptide to be delivered to cortical neurons efficiently and without toxicity, the chromophore fluorescein isothiocyanate was conjugated to the tat-HIF/ODD/Wt peptide. Tat-HIF/ODD/Wt/FITC peptides (10 µM) were bath applied to rat cortical neuronal cultures from E17 rat embryos. These cultures are approximately 90% neurons after one day in vitro. The balance of the cells in the culture is glial in origin.

Twenty-four hours after addition of the peptide to the bathing medium, the level of intracellular accumulation of the peptide was monitored by fluorescence microscopy. In every field examined (>10), each cell nucleus, identified by DNA intercalating chromophore DAPI, was found to be associated with fluorescence label in its cell bodies and processes reflecting the uptake of the Tat-HIF/ODD/wt FITC peptide. Similar high efficiency transduction was observed when cortical neuronal cultures were incubated with the Tat-HIF/ODD/mut FITC peptide. In parallel, viability measurements verified that the Tat-HIF/ODD peptides do not negatively alter basal viability in our cortical neuronal cultures.

To determine whether the Tat-HIF/ODD/wt peptide stabilizes HIF-1 leading to activation of HIF-1 dependent gene expression, the levels of a luciferase reporter gene that is regulated by a hypoxia response element found in the enolase gene promoter was monitored. The addition of Tat-HIF/ODD/wt peptide significantly enhanced levels of a hypoxia response element regulated reporter gene in a concentration dependent manner.

Figure 5:
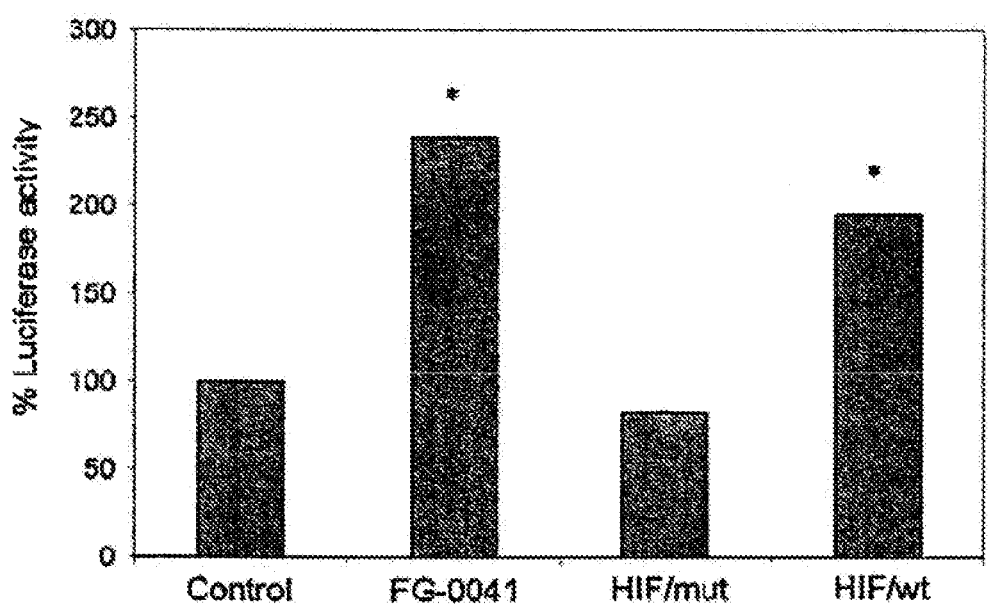
FIG. 5. A cell permeant, peptide inhibitor of the HIF prolyl 4-hydroxylase, but not a mutant control, induces expression of HIF-dependent genes. Tat-HIF/wt peptide (100 µM) but not a corresponding peptide with the C-terminal proline hydroxylation site of HIF-1α mutated (Tat-HIF/mut, 100 µM) significantly enhances the activity of a hypoxia response element driven reporter in cortical neurons (* corresponds to $p<0.05$ compared to control by paired T-test). The low molecular weight P4H inhibitor, FG-0041 (40 µM) was used as a positive control.

The level of induction of the HIF-dependent reporter gene by 100 µM Tat-HIF/ODD/wt peptide was similar to that stimulated by 40 µM FG-0041, a low molecular weight inhibitor of the prolyl hydroxylase (FIG. 5). By contrast, 100 µM Tat-HIF/ODD/mut peptide with proline 564 and its adjacent praline mutated to alanine did not induce the HIF-dependent reporter gene.

To verify that the changes in the HIF-dependent reporter gene reflect changes in endogenous HIF-dependent genes, enolase, p21 waf/cip1, and VEGF were monitored by RT-PCR. β-actin was measured as a control. As expected, the Tat-HIF/ODD/wt peptide increased levels of enolase, p21 waf1/Cip1 and VEGF message but did not alter levels of β-actin. The Tat-HIF/ODD/mut did not affect levels of p21 waf1/cip or β-actin and actually diminished the basal levels of enolase and VEGF, two known HIF-dependent genes. Taken together, these results establish that the Tat-HIF/ODD wt peptide can be delivered to neurons and can enhance the transcriptional activity of well characterized HIF target genes. By contrast, a Tat/HIF/ODD mut in which the conserved proline hydroxylation site (proline 564) and an adjacent proline have been mutated to alanine does not upregulate a HIF-dependent reporter gene or endogenous HIF regulated genes (e.g., enolase, p21 waf1/cip1/or VEGF).

Figure 6:
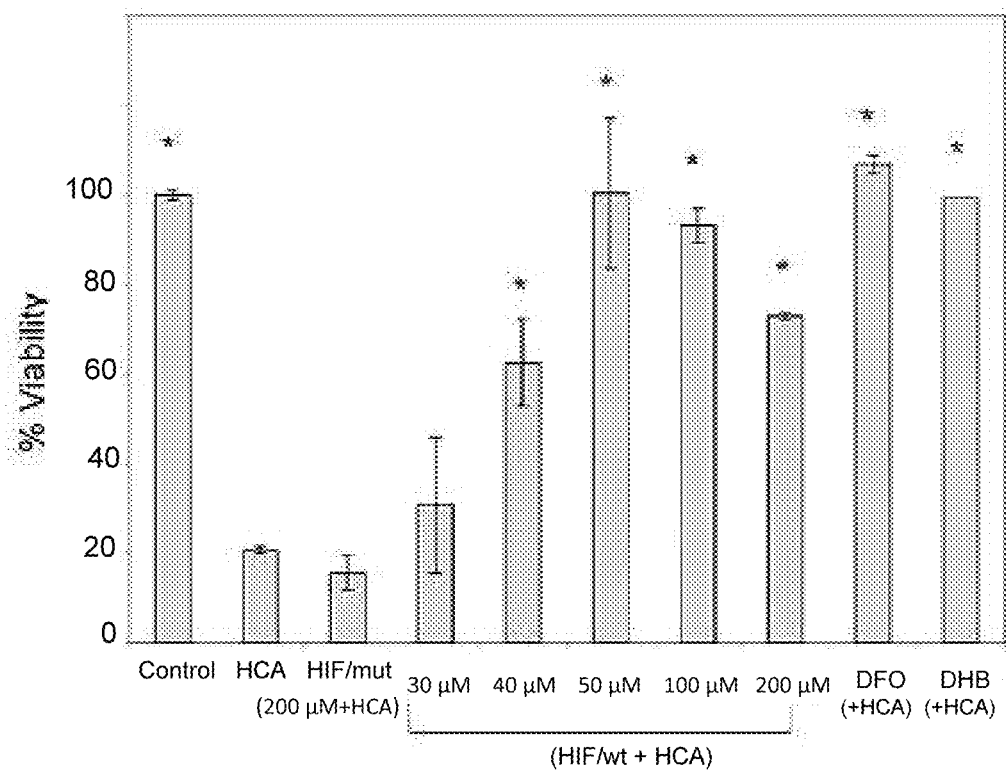
FIG. 6. A cell permeant, peptide inhibitor of the HIF 4-hydroxylase, but not a mutant control, prevents oxidative glutamate toxicity. The glutamate analog, homocysteate (HCA) (5 mM) was added to cortical neurons (1 DIV) with or without Tat-HIF/wt peptide (30, 40, 50, 100 and 200 µM), Tat-HIF/mut peptide (200 µM), DFO (100 µM) and 3,4 DHB (10 µM). Twenty-four hours later cell viability was determined using the MTT assay. Graph depicts mean+/−SE for three experiments performed in triplicate (* denotes $p<0.05$ from HCA treated cultures by ANOVA and Student-Newman Keuls tests for control, Tat-HIF/wt, Tat-HIF/mut, DFO and 3,4 DHB).

To test whether Tat-HIF/ODD/wt can prevent oxidative neuronal death in cortical neurons induced the glutamate analog, HCA, the peptides were applied 24 hours prior to the addition of HCA. Addition of tat-HIF/ODD/wt peptide but not its mutant control (tat-HIF/ODD/mut) protected cortical neurons from oxidative glutamate toxicity in a concentration dependent manner as assessed by MTT assay (FIG. 6). The morphology of the neurons that were protected from oxidative glutamate toxicity by Tat-HIF/ODD/wt was indistinguishable from the morphology of control neurons as assessed by phase contrast microscopy or calcein/ethidium homodimer staining (not shown). These results suggest that inhibition of HIF Prolyl 4 Hydroxylases prevents oxidative neuronal death in cortical neurons in vitro dioxygenase.

What is claimed is:

1. A method for enhancing hypoxia inducible factor (HIF) activity in a cell in need thereof, the method comprising contacting the cell with any one of the following compounds: 3,6-bis[2-(dimethylamino)ethoxy]-9h-xanthen-9-onedihydrochloride (R-10,874-DA), 2,8-bis[dimethylaminoacetyl]dibenzofurin dihydrochloride hydrate (R-11,567-DA), a tilorone analogue R-9536-DA and HIF alpha protein fused to a carrier peptide.

2. A method according to claim 1, wherein the carrier peptide is tat.

3. A method according to claim 1, wherein the carrier peptide is an aromatic-cationic peptide.

4. A method for treating stroke in a mammal in need thereof, the method comprising administering to the mammal any one of the following compounds: 3,6-bis[2-(dimethylamino)ethoxy]-9h-xanthen-9-onedihydrochloride (R-10,874-DA), 2,8-bis[dimethylaminoacetyl]dibenzofurin dihydrochloride hydrate (R-11,567-DA) and a tilorone analogue R-9536-DA.

5. A method according to claim 1 wherein the compound is selected from the group consisting of R-9536-DA, R-10,874-DA and R-11,567-DA.

* * * * *

UNITED STATES PATENT AND TRADEMARK OFFICE
CERTIFICATE OF CORRECTION

| | | |
|---|---|---|
| PATENT NO. | : 9,795,587 B2 | Page 1 of 1 |
| APPLICATION NO. | : 14/575387 | |
| DATED | : October 24, 2017 | |
| INVENTOR(S) | : Rajiv Ratan et al. | |

It is certified that error appears in the above-identified patent and that said Letters Patent is hereby corrected as shown below:

In the Specification

Column 1, Lines 14-20:
Now reads:
"The invention described in this application was made with funds from the National Institutes of Health, Grant Numbers NS 39170, NS 40591, and NS 46239. The United States Government has certain rights in this invention.
The invention was also made with funds from New York State, contract number CO19772.
New York State has certain rights in this invention."
Should read:
-- "STATEMENT REGARDING FEDERALLY SPONSORED RESEARCH OR DEVELOPMENT
This invention was made with government support under NS039170, NS040591 & NS046239 awarded by the National Institutes of Health. The government has certain rights in the invention." --

Signed and Sealed this
Fifteenth Day of May, 2018

Andrei Iancu
*Director of the United States Patent and Trademark Office*

```
                        SEQUENCE LISTING

<160> NUMBER OF SEQ ID NOS: 5

<210> SEQ ID NO 1
<211> LENGTH: 826
<212> TYPE: PRT
<213> ORGANISM: Homo sapiens

<400> SEQUENCE: 1

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
```

-continued

```
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
            355                 360                 365
Met Lys Met Thr Gln Leu Phe Thr Lys Val Glu Ser Glu Asp Thr Ser
        370                 375                 380
Ser Leu Phe Asp Lys Leu Lys Lys Glu Pro Asp Ala Leu Thr Leu Leu
385                 390                 395                 400
Ala Pro Ala Ala Gly Asp Thr Ile Ile Ser Leu Asp Phe Gly Ser Asn
                405                 410                 415
Asp Thr Glu Thr Asp Asp Gln Gln Leu Glu Glu Val Pro Leu Tyr Asn
                420                 425                 430
Asp Val Met Leu Pro Ser Pro Asn Glu Lys Leu Gln Asn Ile Asn Leu
            435                 440                 445
Ala Met Ser Pro Leu Pro Thr Ala Glu Thr Pro Lys Pro Leu Arg Ser
        450                 455                 460
Ser Ala Asp Pro Ala Leu Asn Gln Glu Val Ala Leu Lys Leu Glu Pro
465                 470                 475                 480
Asn Pro Glu Ser Leu Glu Leu Ser Phe Thr Met Pro Gln Ile Gln Asp
                485                 490                 495
Gln Thr Pro Ser Pro Ser Asp Gly Ser Thr Arg Gln Ser Ser Pro Glu
            500                 505                 510
Pro Asn Ser Pro Ser Glu Tyr Cys Phe Tyr Val Asp Ser Asp Met Val
            515                 520                 525
Asn Glu Phe Lys Leu Glu Leu Val Glu Lys Leu Phe Ala Glu Asp Thr
        530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
            595                 600                 605
Glu Pro Thr Ala Asn Ala Thr Thr Thr Thr Ala Thr Thr Asp Glu Leu
        610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
                660                 665                 670
Gly Lys Gly Val Ile Glu Gln Thr Glu Lys Ser His Pro Arg Ser Pro
            675                 680                 685
Asn Val Leu Ser Val Ala Leu Ser Gln Arg Thr Thr Val Pro Glu Glu
        690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                725                 730                 735
Leu Leu Gln Gln Pro Asp Asp His Ala Ala Thr Thr Ser Leu Ser Trp
            740                 745                 750
```

```
Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
        770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 2'6' dimethyltyrosine
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: AMIDATION

<400> SEQUENCE: 2

Tyr Arg Phe Lys Cys
1               5

<210> SEQ ID NO 3
<211> LENGTH: 19
<212> TYPE: PRT
<213> ORGANISM: Homo sapiens

<400> SEQUENCE: 3

Asp Asp Leu Asp Glu Met Leu Ala Pro Tyr Ile Pro Met Asp Asp Asp
1               5                   10                  15

Phe Gln Leu

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Asp Asp Leu Glu Met Leu Ala Ala Tyr Ile Ala Met Asp Asp Asp Phe
1               5                   10                  15

Gln Leu

<210> SEQ ID NO 5
<211> LENGTH: 11
```

```
<212> TYPE: PRT
<213> ORGANISM: Human immunodeficiency virus type 1

<400> SEQUENCE: 5

Tyr Gly Arg Lys Lys Lys Arg Arg Gln Arg Arg
1               5                   10
```